(12) United States Patent
Fu et al.

(10) Patent No.: US 10,768,161 B2
(45) Date of Patent: Sep. 8, 2020

(54) METHOD FOR ECOLOGICAL RISK ASSESSMENT OF HEAVY METAL IN RIVER BASIN SEDIMENT BASED ON TOXICITY EFFECT

(71) Applicant: CHINESE RESEARCH ACADEMY OF ENVIRONMENTAL SCIENCES, Beijing (CN)

(72) Inventors: Zhiyou Fu, Beijing (CN); Fengchang Wu, Beijing (CN); Lulu Chen, Beijing (CN); Yingchen Bai, Beijing (CN); Chenglian Feng, Beijing (CN); Haiqing Liao, Beijing (CN); Wenjing Guo, Beijing (CN); Huixian Li, Beijing (CN)

(73) Assignee: CHINESE RESEARCH ACADEMY OF ENVIRONMENTAL SCIENCES, Beijing (CN)

( * ) Notice: Subject to any disclaimer, the term of this patent is extended or adjusted under 35 U.S.C. 154(b) by 316 days.

(21) Appl. No.: 16/067,575

(22) PCT Filed: Nov. 1, 2016

(86) PCT No.: PCT/CN2016/104225
§ 371 (c)(1),
(2) Date: Jun. 29, 2018

(87) PCT Pub. No.: WO2017/113980
PCT Pub. Date: Jul. 6, 2017

(65) Prior Publication Data
US 2019/0004024 A1    Jan. 3, 2019

(30) Foreign Application Priority Data
Dec. 30, 2015  (CN) .......................... 2015 1 1018338

(51) Int. Cl.
*G01N 33/24* (2006.01)
*G01N 15/06* (2006.01)
(Continued)

(52) U.S. Cl.
CPC ............. *G01N 33/24* (2013.01); *G01N 15/06* (2013.01); *G16H 50/30* (2018.01); *G06F 17/18* (2013.01)

(58) Field of Classification Search
CPC ........ G01N 33/24; G01N 15/06; G16H 50/30; G06F 17/18
See application file for complete search history.

(56) References Cited

U.S. PATENT DOCUMENTS 6,699,707 B1    3/2004 Hince
2014/0188495 A1*  7/2014 Bi .......................... G06Q 50/22
                                                 705/2
(Continued)

FOREIGN PATENT DOCUMENTS

CN      1987477       6/2007
CN    103793580       5/2014
(Continued)

OTHER PUBLICATIONS

International search report dated Jan. 25, 2017 from corresponding application No. PCT/CN2016/104225.
(Continued)

*Primary Examiner* — Manuel L Barbee
(74) *Attorney, Agent, or Firm* — JCIPRNET

(57) ABSTRACT

A method for determining ecological risk, particularly a method for the ecological risk assessment of a heavy metal in a river basin sediment based on a toxicity effect. The assessment method includes screening the main aquatic organisms in a river basin; sampling a sediment, and determining and detecting the heavy metal type; measuring the (Continued)

concentration of the heavy metal in the sediment; collecting the heavy metal release coefficient; collecting the heavy metal toxicity data and fitting the data; determining the heavy metal $HC_s^i$ value according to a fitting equation; calculating the heavy metal toxicity response coefficient; calculating the ecological risk index of the heavy metal. This method can further include calculating the comprehensive ecological risk index of various types of heavy metals. The method can accurately reflect the ecological risk of a heavy metal on aquatic organisms in a river basin.

9 Claims, 1 Drawing Sheet

(51) Int. Cl.
*G06F 17/18* (2006.01)
*G16H 50/30* (2018.01)

(56) References Cited

U.S. PATENT DOCUMENTS

| | | | |
|---|---|---|---|
| 2016/0025698 A1* | 1/2016 | Qu | G01N 33/1833 |
| | | | 702/25 |
| 2016/0110835 A1* | 4/2016 | Wu | G01N 33/24 |
| | | | 705/325 |

FOREIGN PATENT DOCUMENTS

| | | |
|---|---|---|
| CN | 103793620 | 5/2014 |
| CN | 103886217 | 6/2014 |
| CN | 104636627 | 5/2015 |
| CN | 105608324 | 5/2016 |

OTHER PUBLICATIONS

Chinese First Search report from corresponding application No. CN 201511018338.0.

* cited by examiner

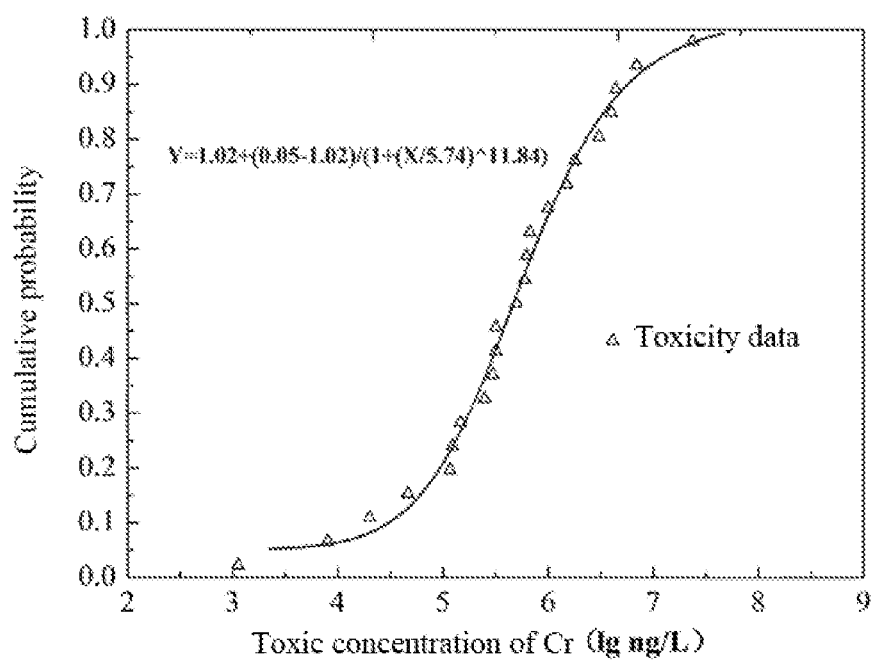

US 10,768,161 B2

METHOD FOR ECOLOGICAL RISK ASSESSMENT OF HEAVY METAL IN RIVER BASIN SEDIMENT BASED ON TOXICITY EFFECT

RELATED APPLICATIONS

The present application is a National Phase of International Application Number PCT/CN2016/104225, filed Nov. 1, 2016, and claims the priority of China Application No. 201511018338.0, filed Dec. 30, 2015.

TECHNICAL FIELD

The present invention relates to a method for determining ecological risk, particularly a method for the ecological risk assessment of heavy metal in a river basin sediment based on toxicity effect.

BACKGROUND ART

Heavy metal pollutants are different from other organic pollutants. Many organic pollutants can be reduced or eliminated through physical, chemical or biological purification of the natural world. Heavy metal pollutants are difficult to be degraded in the environment, causing great harms to the ecological environment and human health and having potential environmental risks. Industrial and agricultural activities generate a large amount of wastes containing heavy metals. The heavy metals enter rivers, lakes and other bodies of water through processes such as migration and release, and most of them are rapidly transferred to sediments and suspended matters. Suspended matters will also gradually become part of the sediments as they are transported by the water stream. The content of heavy metals in sediments is usually much higher than that in water bodies and will gradually be released as the main endogenous source of metal pollutions in water bodies with the changes of environmental conditions. In addition, the distribution of heavy metal content in water is irregular, but it shows a clear horizontal distribution in sediments. The study of heavy metals in sediments can help to trace pollution sources and to understand the diffusion and potential environmental risks of heavy metals. The sediment area is a place where fish, shrimp, shellfish and other benthic animals carry out metabolism. Through the food chain, heavy metals in sediments can be enriched ten thousand times in benthic animals, which is very harmful to aquatic environment ecosystem. Therefore, it is of great significance to study the ecological risk of heavy metals in sediments.

The ecological risk of heavy metals in sediments depends not only on their content, but also on their release from sediments into water bodies, and more directly on their toxic effects on organisms. In particular, when assessing the ecological risk of multiple heavy metals, heavy metals' toxic coefficients need to be introduced due to the different toxic effects of each heavy metal. Moreover, the toxic effects are also affected by biological species, and the biological species are differently distributed in different watersheds.

At present, the ecological risk assessment of heavy metals in sediments is usually evaluated for single metal, such as the method of enrichment factor and geoaccumulation index. However, there are few comprehensive evaluations for multiple metals, such as Excess after Regression Analysis method. Most of these methods do not consider the biotoxicity of heavy metals. Only the potential ecological risk index (RI) proposed by a Swedish scientist, Hakanson, in 1980, comprehensively evaluates the ecological risk of various heavy metals and considers the biotoxicity of different heavy metals on organisms. However, due to the lack of toxicity data of heavy metals at that time, Hakanson calculated the toxicity coefficients of heavy metals indirectly according to the abundance of heavy metals in the earth's crust. He did not calculate the toxicity coefficients of heavy metals on organisms directly, nor did he take into account the sensitivity of different species to heavy metals.

At present, Hakanson's method is still the main method to assess the ecological risk of heavy metals in the field of environmental science and engineering. Patent application CN201410137454.3 discloses "a method for determining ecological risk of heavy metal pollutions in river and lake sediments". This patent application mainly uses the principle of statistics and sampling calculation to determine the distribution of various heavy metals, in which the toxicity coefficient of heavy metal pollutants is still based on the calculation of its crustal abundance. Patent application CN201410074703.9 discloses "a method for comprehensive ecological risk assessment of heavy metal pollutions in three phase space of rivers". This patent application also uses Hakanson's method directly to calculate the toxicity coefficient of heavy metals.

The method proposed by Hakanson is based on the abundance of heavy metals in the earth's crust to calculate the toxicity coefficient of heavy metals, which is a compromise due to the lack of toxicity data for heavy metals at that time. In addition, the existing methods for ecological risk assessment of heavy metals in sediments still lack consideration of the toxic effects of heavy metals on aquatic organisms, and do not take into account the differences in the distribution of biota in different watersheds.

Today, as the toxicity data of heavy metals is more and more complete, the assessment of the ecological risk of heavy metals in sediments urgently requires a more accurate method for calculating the toxicity coefficients of heavy metals in order to evaluate the ecological risk of heavy metals in sediments more accurately.

DISCLOSURE OF THE INVENTION

In order to solve the above problems, the present invention proposes an ecological risk assessment method for heavy metals in river basin sediments based on toxicity effects:

(1) screening the main aquatic species of the assessed river basin environment according to the breadth and quantity of biodistribution;

(2) sampling sediments within the assessed basin area, determining the types of the heavy metals to be detected and numbering them: when there are n kinds of heavy metals to be detected, these heavy metals are numbered 1, 2, ..., n−1, n, wherein $1 \leq n \leq 45$;

(3) measuring the concentration of the $i^{th}$ metal of each sediment sample one by one, and calculating the average concentration $c_{0-1}{}^i$ of the $i^{th}$ heavy metal, and calculating the pollution coefficient $c_f^i$ of the $i^{th}$ heavy metal one by one according to the formula $c_f^i = (c_{0-1}{}^i)/(c_n{}^i)$, wherein, $c_n{}^i$ is the reference value of the $i^{th}$ heavy metal content in uncontaminated sediments;

(4) collecting the release coefficient $c_s{}^i$ of the $i^{th}$ heavy metal;

(5) collecting the chronic toxicity data of the $i^{th}$ heavy metal on aquatic species selected in step (1), performing curve fitting on the collected data, and selecting the curve regression equation with the highest goodness of fit, so as to obtain the best equation for the sensitivity of the $i^{th}$ heavy metal;

(6) drawing a fitting curve (Species Sensitivity Distributions, SSD) according to the best fitting equation obtained in step (5), and setting the y value of this equation, that is, the cumulative probability to 0.05, and then calculating the corresponding x value, which is the toxic concentration $HC_5^i$ of the $i^{th}$ heavy metal that protects 95% of aquatic organisms;

(7) repeating steps (4) to (6) n times to obtain the release coefficient $c_s^i$ and toxic concentration $HC_5^i$ of each heavy metal determined in step (2), and integrating and normalizing the release coefficient $c_s^i$ and toxic concentration $HC_5^i$ of each heavy metal to obtain the toxicity coefficient $S^i$ of the $i^{th}$ heavy metal;

(8) calculating the toxicity response coefficient $Tr^i$ of the $i^{th}$ heavy metal according to the formula $Tr^i=S^i*(5/BPI)^X$ one by one, where BPI is the biological yield index of the water body evaluated and the value of x is 1, ½ or 0;

(9) calculating the ecological risk index $Er^i$ of the $i^{th}$ heavy metal according to the formula $Er^i=Tr^i*c_f^i$ one by one, and the resulting $Er^i$ is used to evaluate the ecological risk of a single metal to the assessed river basin: when $Er^i<30$, the ecological hazard of the $i^{th}$ heavy metal to the assessed river basin is slight, when $30 \le Er^i<60$, the ecological hazard of the $i^{th}$ heavy metal to the assessed river basin is medium, when $60 \le Er^i<120$, the ecological hazard of the $i^{th}$ heavy metal to the assessed river basin is strong, when $120 \le Er^i<240$, the ecological hazard of the $i^{th}$ heavy metal to the assessed river basin is very strong, when $Er^i>240$, the ecological hazard of the $i^{th}$ heavy metal to the assessed river basin is extremely strong.

Preferably, the ecological assessment method described above also includes the step (10), that is using the formula $RI=\Sigma_{i=1}^{N} Er^i$ to calculate the total ecological risk comprehensive index RI caused by multiple heavy metal pollutants in the water body and then using RI to evaluate the ecological risk of the assessed river basin: when $RI<150$, there is a slight ecological hazard in the river basin, when $150 \le RI<300$, there is a medium ecological hazard in the river basin, when $300 \le RI<600$, there is a very strong ecological hazard in the river basin, when $RI \ge 600$, there is an extremely strong ecological hazard in the river basin.

Preferably, the main aquatic species screened in step (1) should be statistically representative, that is, the response of the selected species to the detected heavy metals can represent the response of the ecosystem of the assessed river basin to the detected heavy metals. Therefore, screening needs to be performed in different types of biota, and multiple biological species should be screened in each category of biota. For example, the aquatic organisms include phytoplankton, aquatic plants, zooplankton, fishes, and benthic animals, three biological species should be selected from the above five categories of biota during screening.

Preferably, the sediment samples described in step (2) should be statistically representative: collecting samples from the surface of the sediment at 0-1 cm; the collection points of the samples should be evenly distributed in the assessed river basin; the number of the samples should be determined based on the actual basin area; the larger the basin area, the more samples should be taken; the number of samples is at least five; and the average of its metal concentration is taken.

As we all know, heavy metals refer to metals with specific gravity (density) greater than 4 or 5. There are about 45 kinds of heavy metals, such as Cu, Pb, Zn, Fe, Co, Ni, V, Nb, Ta, Ti, Mn, Cd, Hg, W, Mo, Au, and Ag. Therefore, n in step (2) is defined as $1 \le n \le 45$.

However, the types of the heavy metals described in step (2) should be determined based on the main sources of the pollutions in the river basin. Preferably, based on the current status of pollutions in China's river basin and the realization and popularization of precise testing methods, it is commended that the tested heavy metals include at least the following eight toxic heavy metals: Hg, Cd, Pb, Cu, Zn, Cr, As, Ni, that is, $n \ge 8$.

Preferably, the reference value $c_n^i$ of the $i^{th}$ heavy metal content in uncontaminated sediments described in step (3), that is, the highest background value of the global sediment metals before industrialization, which can be obtained from the existing literature (for example, "Calculation of heavy metals' toxicity coefficient in the evaluation of potential ecological risk index", Environmental Science and Technology, Vol. 31, No. 2).

Preferably, plotting the collected concentration values of toxicity data for different species of organisms against the quantiles arranged in concentration, and selecting the curve equation to fit based on the resulting data point distribution shape. The fitting should adopt several different functions and select the optimal regression curve, so as to avoid the systematic errors introduced by improper selection of functions. When the distribution of the toxicity data points is a common S-type, the fitting curves are preferred to use the log-Normal distribution function, the log-logistic distribution function, the log-triangular distribution function, or a combination thereof. When the distribution of the toxicity data points is different from the common S-type distribution, other curves or non-parametric methods can be used to fit the data points, for example, using the Burr type III distribution function as the regression curve equation of the toxicity data of heavy metals.

Preferably, the goodness of fit described in step (5) is determined by the toxicity data points and the judgment coefficient $R^2$ of the resulting curve regression equation: when the judgment coefficient $R^2$ of the curve regression equation gets closer to 1, the goodness of the curve regression equation for the data is higher. When several judgment coefficients obtained above are very close, using the toxicity data points and the estimated standard error $S_{xy}$ of the obtained curve regression equation to further judge the goodness of fit of the selected curve equation: the smaller the estimated standard error $S_{xy}$ of the curve regression equation, the higher the goodness of fit of this curve regression equation.

Preferably, the concentration $HC_5^i$ of the $i^{th}$ heavy metal that protects 95% of aquatic organisms described in step (6) is the toxicity data corresponding to the cumulative probability of 5% aquatic organisms on the fitted curve. In general, when the concentration of heavy metals is lower than this reference value, most aquatic organisms can be protected, making the entire ecosystem sustainable.

Preferably, the integrating and normalizing regulation described in step (7) comprises the following calculation steps:

a. calculating the reciprocal of the concentration $HC_5^i$ of the $i^{th}$ heavy metal, and keeping three significant figures for each value obtained;

b. dividing each reciprocal number obtained in step a by the smallest one of them, and keeping three significant figures for each value obtained;

c. multiplying each value obtained in step b by the release coefficient $c_s^i$ of the corresponding $i^{th}$ heavy metal;

d. dividing each value obtained in step c by the smallest one of them, and keeping three significant figures for each value obtained;

e. squaring the values obtained in step d, and keeping two significant figures for each value obtained.

Preferably, the BPI described in step (8) is the bioproduction index, which is determined by the burning amount and nitrogen content of the sediment samples. BPI indicates the sensitivity of water to heavy metal pollutions, namely the effects of Eh and pH of pore water in sediments, and pH, salinity, and alkalinity of overlying water on the various heavy metals in the water.

Preferably, the value of x described in step (8) is determined by the type of heavy metals that is measured. The toxicity response coefficient of Hg decreases with the increase of BPI, and the relationship between them is linear. Therefore, when the measured metal is Hg, the value of x is 1. The toxicity response coefficient of As is independent of BPI. Therefore, when the measured metal is As, the value of x is 0. The toxicity response coefficient of other heavy metals also decreases with the increase of BPI, but it is not linear. Therefore, when the measured metal is not Hg or As, the value of x is ½.

Compared with the prior art, the advantages of the method for ecological risk assessment of heavy metal in river basin sediment based on toxicity effect provided by the present invention are as follows:

1. The actual toxic effect data of metals on aquatic organisms is used, and the toxicity susceptibility of metals to different species is taken into account. The threshold value for protection of 95% of organisms is used to determine the toxicity coefficient of metals, and the concept of risk is introduced to the determination of toxicity coefficient. Compared with the prior art that uses the abundance of the earth's crust to measure the toxic effect of metals, the ecological risk assessment method provided by the present invention can more accurately reflect the risk of heavy metals in sediments to aquatic organisms and the ecology of the assessed river basin.

2. The toxicity coefficient of heavy metals in the method for ecological risk assessment of heavy metal in river basin sediment based on toxicity effect is calculated based on the biota distribution of the river basin. When the distribution of the biota in the river basin has a certain representativeness, the toxicity coefficient of heavy metals calculated in step (7) of the present invention can be used as a reference value of the toxicity coefficient of heavy metals to evaluate other basins with similar biota distributions without recalculating the toxicity coefficient of heavy metals. For example, when the river basin is a typical shallow plain lake in eastern China, the toxicity coefficient obtained by step (7) of the present invention can be used as a reference value for evaluating other plain shallow lakes in eastern China.

BRIEF DESCRIPTION OF THE DRAWINGS

FIG. 1: Curve of the toxicity data of Cr in example 1.

DETAILED DESCRIPTION OF THE PREFERRED EMBODIMENT

The embodiments of the present invention are described in detail below, and examples of the embodiments are shown in the accompany drawings. The embodiments described with reference to the drawings are exemplary, which are used to explain the present invention only, and should not be construed as limiting the present invention.

Example 1

Assessing the ecological risk of heavy metals in a lake basin sediment:

1. screening the main aquatic species of the assessed basin environment according to the breadth and quantity of biodistribution; the main aquatic species comprise: pyrrophyta, *scenedesmus* and cryptophyta belonging to phytoplankton, wild lotus, duckweed and Azolla *pinnata* belonging to hydrophyte, Arenaceous sanding, Brachionus calyciflorus and bosmina belonging to zooplankton, Protosalanx hyalocranius, carp and Coilia nasus *taihuensis* belonging to fish, *Corbicula fluminea*, chironomus and Bellamya *aeruginosa* belonging to zoobenthos;

2. sampling sediments within the assessed basin area, determining the types of heavy metals to be detected and numbering them: when there are 8 kinds of heavy metals to be detected, these heavy metals are numbered Cr(1), Ni(2), Cu(3), Zn(4), As(5), Cd(6), Hg(7) and Pb(8);

3. measuring the concentration of the $i^{th}$ metal of each sediment sample one by one, and calculating the average concentration $c_{0-1}{}^i$ of the $i^{th}$ heavy metal, and calculating the pollution coefficient $c_f^i$ of the heavy metal one by one according to the formula $c_f^i=(c_{0-1}{}^i)/(c_n{}^i)$, where $c_n{}^i$ is the content of the $i^{th}$ heavy metal in sediments that are uncontaminated(that is, pre-industrial and pre-modern civilization); the specific value of $c_n{}^i$ is obtained from the literature: "Calculation of heavy metals' toxicity coefficient in the evaluation of potential ecological risk index", Environmental Science and Technology, Vol. 31, No. 2; the data obtained in this step is shown in Table 1;

4. collecting the release coefficient $c_s^1=2\times10^{-3}$ of the first heavy metal (Cr) form the literature;

5. collecting the chronic toxicity data of Cr on aquatic species selected in step (1) and plotting the collected concentration values of toxicity data against the quantiles arranged in concentration; the result shows that the distribution of data points is S-shape, so the data points are fitted using the log-Normal distribution function, the log-logistic distribution function and the log-triangular distribution function; the judgment coefficient $R^2$ of the log-logistic distribution fitting equation is the closest to 1 compared to the other two distribution function fitting equations, so the log-logistic distribution function fitting equation is selected as the optimal fitting equation, that is, $Y=1.02+(0.05-1.02)/(1+(X/5.74)^\wedge 11.84$; the collected data is shown in Table 2, and the curve obtained is shown in FIG. 1;

6. setting the value of y of the best-fitting equation obtained in step 5 to 0.05, and calculating the corresponding value of x, that is, the toxic concentration $HC_5^i$ of Cr that protects 95% of aquatic organisms; the value obtained is 2.42 µg/L;

7. repeating steps 4 to 6 n times to obtain the release coefficient $c_s^i$ and toxic concentration $HC_5^i$ of each heavy metal determined in step (2), and integrating and normalizing the release coefficient $c_s^i$ and toxic concentration $HC_5^i$ of each heavy metal to obtain the toxicity coefficient $S^i$ of the $i^{th}$ heavy metal; the toxic concentration $HC_5^i$ obtained in this step and the data generated in the integration and normalization are shown in Table 3;

8. calculating the toxicity response coefficient $Tr^i$ of the $i^{th}$ heavy metal according to the formula $Tr^i=S^i*(5/BPI)^X$ one by one, where BPI is the biological yield index of the evaluated water body and is determined by the burning amount and nitrogen content of the sediment samples; by this method, the lake's BPI=6.7, the value of x is 1, ½ or 0; the toxicity response coefficient of the $i^{th}$ heavy metal obtained in this step is shown in Table 4;

9. calculating the ecological risk index $Er^i$ of the $i^{th}$ heavy metal according to the formula $Er^i=Tr^i*c_f^i$ one by one; the ecological risk index of the $i^{th}$ heavy metal obtained in this step is shown in Table 4; the data in Table 4 shows that, among the tested 8 heavy metals, only Hg has a medium ecological hazard to the lake, and the remaining 7 heavy metals have a slight ecological hazard;

10. using the formula $RI=\Sigma_{i=1}^{N} Er^i$ to calculate the total ecological risk comprehensive index RI, which is caused by multiple heavy metal pollutants in the water body and then using RI to evaluate the ecological risk of the assessed basin; the value of RI is 114, which indicates that the comprehensive ecological hazard caused by the assessed 8 heavy metals on this lake is slight.

TABLE 2

The chronic toxicity data of Cr

| Taxa | Species | Toxicity endpoint | Toxicity data (µg/kg) |
|---|---|---|---|
| Phytoplankton | Pyrrophyta | NOEC | 671 |
| | Scenedesmus | NOEC | 8 |
| | Cryptophyta | NOEC | 317 |
| Hydrophyte | Wild lotus | NOEC | 123 |
| | Duckweed | NOEC | 1000 |
| | Azolla pinnata | NOEC | 625 |
| Zooplankton | Arenaceous sanding | NOEC | 1500 |
| | Brachionus calyciflorus | NOEC | 1789 |
| | Bosmina | NOEC | 46.5 |
| Fishes | Protosalanx hyalocranius | NOEC | 4405 |
| | Carp | NOEC | 23516 |
| | Coilia nasus taihuensis | NOEC | 6941 |
| Zoobenthos | Corbicula fluminea | NOEC | 1.13 |
| | Chironomus | NOEC | 20 |
| | Bellamya aeruginose | NOEC | 250 |

TABLE 3

Integration and normalization of the toxicity coefficient $S^i$ of each heavy metal

| | Cr | Ni | Cu | Zn | As | Cd | Hg | Pb |
|---|---|---|---|---|---|---|---|---|
| Toxic concentration | 2.42 | 6.03 | 0.89 | 10.83 | 14.9 | 0.3 | 0.53 | 22 |
| Reciprocal | 0.413 | 0.166 | 1.12 | 0.0923 | 0.0671 | 3.33 | 1.89 | 0.0455 |
| Divided by the smallest number | 9.08 | 3.65 | 24.6 | 2.03 | 1.48 | 73.2 | 41.5 | 1 |
| Release coefficient | 2 | 147 | 200 | 57 | 27 | 200 | 320 | 71 |
| Multiplying $HC_5$ by release coefficient | 18.16 | 536.55 | 4920 | 115.71 | 39.96 | 14640 | 13280 | 71 |
| Divided by the smallest number | 1 | 29.6 | 271 | 6.37 | 2.2 | 806 | 731 | 3.91 |
| Square root | 1 | 5.5 | 17 | 2.5 | 1.5 | 28 | 27 | 2 |

TABLE 1

The concentration and the pollution coefficient of heavy metals in the lake sediments

| | Cr | Ni | Cu | Zn | As | Cd | Hg | Pb |
|---|---|---|---|---|---|---|---|---|
| Average concentration in sediments (µg/kg) | 70.92 | 55.28 | 91.15 | 215.64 | 10.52 | 0.76 | 0.676 | 248.57 |
| Content in uncontaminated sediments (µg/kg) | 90 | 68 | 50 | 175 | 15 | 1 | 0.25 | 70 |
| pollution coefficient | 0.79 | 0.81 | 1.82 | 1.23 | 0.70 | 0.76 | 2.70 | 3.55 |

TABLE 4

Toxicity response coefficient of each heavy metal

| | Cr | Ni | Cu | Zn | As | Cd | Hg | Pb |
|---|---|---|---|---|---|---|---|---|
| Toxicity coefficient | 1.00 | 5.50 | 17.00 | 2.50 | 1.50 | 28.00 | 27.00 | 2.00 |
| Bioproduction index | 6.70 | 6.70 | 6.70 | 6.70 | 6.70 | 6.70 | 6.70 | 6.70 |
| Value of x | 0.50 | 0.50 | 0.50 | 0.50 | 0.00 | 0.50 | 1.00 | 0.50 |
| Toxicity response coefficient | 0.86 | 4.75 | 14.69 | 2.16 | 1.50 | 24.19 | 20.15 | 1.73 |
| Pollution coefficient | 0.79 | 0.81 | 1.82 | 1.23 | 0.70 | 0.76 | 2.70 | 3.55 |
| Pollution risk index | 0.68 | 3.85 | 26.73 | 2.66 | 1.05 | 18.38 | 54.40 | 6.13 |

What is claimed is:

1. A method for ecological risk assessment of heavy metals in river basin sediment based on toxicity effect, the method comprises the following steps:

(1) screening the main aquatic species of the assessed river basin environment according to the breadth and quantity of biodistribution;
(2) sampling sediments within the assessed basin area, determining the types of heavy metals to be detected and numbering them: when there are n kinds of heavy metals to be detected, these heavy metals are numbered 1, 2, . . . , n−1, n, wherein 1≤n≤45;
(3) measuring the concentration of the $i^{th}$ heavy metal of each sediment sample one by one, and calculating the average concentration $c_{0-1}{}^i$ of the $i^{th}$ heavy metal, and calculating the pollution coefficient $c_f{}^i$ of the $i^{th}$ heavy metal one by one according to the formula $c_f{}^i=(c_{0-1}{}^i)/(c_n{}^i)$, wherein, $c_n{}^i$ is the reference value of the $i^{th}$ heavy metal content in uncontaminated sediments;
(4) collecting the release coefficient $c_s{}^i$ of the $i^{th}$ heavy metal;
(5) collecting the chronic toxicity data of the $i^{th}$ heavy metal on aquatic species selected in step (1), performing curve fitting on the collected data, and selecting the curve regression equation with the highest goodness of fit, so as to obtain the best equation for the sensitivity of the $i^{th}$ heavy metal;
(6) drawing a fitting curve (SSD) according to the best fitting equation obtained in step (5), and setting the y value of this equation, that is, the cumulative probability to 0.05, and then calculating the corresponding x value, which is the toxic concentration $HC_s{}^i$ of the $i^{th}$ heavy metal that protects 95% of aquatic organisms;
(7) repeating steps (4) to (6) n times to obtain the release coefficient $c_s{}^i$ and toxic concentration $HC_s{}^i$ of each heavy metal determined in step (2), and integrating and normalizing the release coefficient $c_s{}^i$ and toxic concentration $HC_s{}^i$ of each heavy metal to obtain the toxicity coefficient $S^i$ of the $i^{th}$ heavy metal;
(8) calculating the toxicity response coefficient $Tr^i$ of the $i^{th}$ heavy metal according to the formula $Tr^i=S^i*(5/BPI)^X$ one by one, where BPI is the biological yield index of the water body evaluated and the value of x is 1, ½ or 0;
(9) calculating the ecological risk index $Er^i$ of the $i^{th}$ heavy metal according to the formula $Er^i=Tr^i*c_f{}^i$ one by one, and the resulting $Er^i$ is used to evaluate the ecological risk of a single metal to the river basin: when $Er^i<30$, the ecological hazard of the $i^{th}$ heavy metal to the assessed river basin is slight, when $30<Er^i<60$, the ecological hazard of the $i^{th}$ heavy metal to the assessed river basin is medium, when $60<Er^i<120$, the ecological hazard of the $i^{th}$ heavy metal to the assessed river basin is strong, when $120<Er^i<240$, the ecological hazard of the $i^{th}$ heavy metal to the assessed river basin is very strong, when $Er^i>240$, the ecological hazard of the $i^{th}$ heavy metal to the assessed river basin is extremely strong.

2. The method for ecological risk assessment of heavy metal in river basin sediment based on toxicity effect according to claim 1, wherein, the evaluation method also comprises step (10): using the formula $RI=\Sigma_{i=1}^{N} Er^i$ to calculate the total ecological risk comprehensive index RI caused by multiple heavy metal pollutants in the water body and then using RI to evaluate the ecological risk of the river basin: when RI<150, there is a slight ecological hazard in the basin, when 150≤RI<300, there is a medium ecological hazard in the river basin, when 300≤RI<600, there is a very strong ecological hazard in the river basin, when RI≥600, there is an extremely strong ecological hazard in the river basin.

3. The method for ecological risk assessment of heavy metal in river basin sediment based on toxicity effect according to claim 1, wherein, the sediment sample in step (2) should be statistically representative: the collection points of the samples should be evenly distributed in the assessed basin and the number of samples is at least five.

4. The method for ecological risk assessment of heavy metal in river basin sediment based on toxicity effect according to claim 1, wherein, the type of heavy metals in step (2) should be determined based on the main source of pollutions in the river basin and the tested heavy metals comprise the following kinds: Cr, Ni, Cu, Zn, As, Cd, Hg and Pb.

5. The method for ecological risk assessment of heavy metal in river basin sediment based on toxicity effect according to claim 1, wherein, the curve in step (5) is a log-Normal distribution function, a log-logistic distribution function, a log-triangular distribution function, or a combination thereof.

6. The method for ecological risk assessment of heavy metal in river basin sediment based on toxicity effect according to claim 1, wherein, the goodness of fit in step (5) is determined by the toxicity data points and the judgment coefficient $R^2$ of the resulting curve regression equation: when the judgment coefficient $R^2$ of the curve regression equation gets closer to 1, the goodness of the curve regression equation for the data is higher; using the toxicity data points and the estimated standard error $S_{xy}$ of the obtained curve regression equation to further judge the goodness of fit of the selected curve equation: the smaller the estimated standard error $S_{xy}$ the curve regression equation, the higher the goodness of fit of this curve regression equation.

7. The method for ecological risk assessment of heavy metal in river basin sediment based on toxicity effect according to claim 1, wherein, the integrating and normalizing described in step (7) comprises the following calculation steps:
a. calculating the reciprocal of the concentration $HC_s{}^i$ of the $i^{th}$ heavy metal, and keeping three significant figures for each value obtained;
b. dividing each reciprocal number obtained in step a by the smallest one of them, and keeping three significant figures for each value obtained;
c. multiplying each value obtained in step b by the release coefficient $c_s{}^i$ of the corresponding $i^{th}$ heavy metal;
d. dividing each value obtained in step c by the smallest one of them, and keeping three significant figures for each value obtained;
e. squaring the values obtained in step d, and keeping two significant figures for each value obtained.

8. The method for ecological risk assessment of heavy metal in river basin sediment based on toxicity effect according to claim 7, wherein, the toxicity coefficient of the $i^{th}$ heavy metal obtained in step (7) is as follows:

| Cr | Ni | Cu | Zn | As | Cd | Hg | Pb |
|---|---|---|---|---|---|---|---|
| 1.00 | 5.50 | 17.00 | 2.50 | 1.50 | 28.00 | 27.00 | 2.00. |

9. The method for ecological risk assessment of heavy metal in river basin sediment based on toxicity effect according to claim 1, wherein, the value of x in step (8) is determined by the type of heavy metal that is measured: x takes a value of 1 when Hg is measured; x takes a value of 0 when As is measured; x takes ½ when heavy metals other than Hg or As are measured.

* * * * *